United States Patent [19]

Gervasutti

[11] Patent Number: 4,937,391
[45] Date of Patent: Jun. 26, 1990

[54] PROCESS FOR PREPARING PERFLUORO-(2-BROMOETHYL-VINYL-ETHER)

[75] Inventor: Claudio Gervasutti, Mestre, Italy

[73] Assignee: Ausimont S.r.l., Milan, Italy

[21] Appl. No.: 373,184

[22] Filed: Jun. 29, 1989

[30] Foreign Application Priority Data

Jul. 4, 1988 [IT] Italy ................. 21211 A/88

[51] Int. Cl.$^5$ ............................ C07C 41/24
[52] U.S. Cl. .................... 568/684; 568/685
[58] Field of Search ................. 568/684, 685

[56] References Cited

U.S. PATENT DOCUMENTS 4,340,750 2/1982 Yamabe et al. .......... 568/684

Primary Examiner—Howard T. Mars
Attorney, Agent, or Firm—Stevens, Davis, Miller & Mosher

[57] ABSTRACT

Preparing perfluoro-(2-bromoethyl-vinyl-ether)

$$CBrF_2-CF_2-O-CF=CF_2$$

by the dechlorination of 2-bromo-1',2'-dichloro-perfluorodiethyl-ether $$CBrF_2-CF_2-O-CClF-CClF_2$$

in the presence of copper and a solvent constituted by an aliphatic amide of the formula

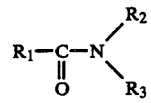

wherein
$R_1$ and $R_2$ are either H or ($C_1$–$C_2$)-alkyl groups and
$R_3$ is a ($C_1$–$C_2$)-alkyl group,
at temperatures within the range of from 100° up to 160° C.

9 Claims, No Drawings

PROCESS FOR PREPARING PERFLUORO-(2-BROMOETHYL-VINYL-ETHER)

DESCRIPTION OF THE INVENTION

The present invention relates to perfluoro-(2-bromoethyl-vinyl-ether) (PFBEVE), which is an interesting compound from a commercial viewpoint, one that e.g. finds application as a comonomer in the preparation of fluoropolymers.

From the relevent technical literature several methods for preparing perfluoro-(2-bromoethylvinylether) are known.

One of the suggested methods (EP-A-No. 0 079 555) consists in reacting tetrafluoroethylene and bromodifluoroacetyl fluoride in the presence of KF and iodine in order to obtain 1-bromo-1,1,2,2,4,4,5,5-octafluoro-5-iodo-3-oxapentane $$CF_2ICF_2OCF_2CF_2Br,$$

this iodo-ether being then subjected to a treatment with Zn and a solvent in order to remove IF according to the reaction:

$$ICF_2CF_2OCF_2CF_2Br \xrightarrow[\text{solvent}]{Zn} CF_2=CFOCF_2CF_2Br + IF$$

However, the above end reaction step does not constitute the object of specific examples, and the end yield of product is not reported.

In U.S. Pat. No. 4,340,750 a process is disclosed for preparing fluorovinylethers of the formula $$XR_fCF_2OCF=CF_2$$

wherein X stands for several substituents, among which are bromine, and $R_f$ represents a bifunctional ($C_1$-$C_{20}$)-perfluoroalkyl group. In this case the end step of the reaction:

$$XR_fCF_2OCF_2CF_2I \rightarrow XR_fCF_2OCF=CF_2$$

involves the presence of a catalyst selected from among a large number of metals, such as Mg, Cu, Zn, Zn—Cu, Zn—Cd, Zn—Pd, Zn—Hg, Sn, Sb and an inert, apolar, aprotic solvent such as benzonitrile, α-naphthonitrile, diphenylether and their mixtures. In this patent, no specific examples are reported in which X is Br and $R_f$ is $CF_2$, and in which Cu and an aliphatic amide are used.

Another method for preparing $$CBrF_2-CF_2-O-CF=CF_2$$

comprises the dechlorination of 2-bromo-1', 2'-dichloro-perfluoro-diethyl-ether $$CBrF_2-CF_2-OCClF-CClF_2.$$

A method for preparing the compound $$CBrF_2-CF_2-O-CClF-CClF_2$$

is disclosed in commonly-owned Italian patent application No. 22,348 A/86, and comprises the reaction of perfluorobromo-ethyl hypofluorite $$CBrF_2CF_2OF$$

with the olefin $$CFCl=CFCl$$

at a temperature within the range of from −40° to −150° C.

The dechlorination reaction of $$CBrF_2-CF_2-O-CClF-CClF_2$$

according to the reaction scheme:

$$CBrF_2-CF_2-O-CClF-CClF_2 \xrightarrow[\text{solvent}]{\text{metal}}$$

$$CBrF_2-CF_2-O-CF=CF_2$$

is a particular type of β-elimination only concerning both adjacent chlorine atoms, with the third halogen (Br) not being involved.

Actually, the selectivity of the above reaction is particularly difficult to be achieved.

In fact, according to the particular metal/solvent pair used, a course of reaction may be observed which is very different from that above stated or it may happen that a reaction does not occur at all (even after long reaction times) or the reaction may lead to different products, according to the following reaction schemes:

$$CBrF_2-CF_2-O-CClF-CClF_2 \xrightarrow{A}$$

$$CBrF_2-CF_2-O-CF=CF_2 \xrightarrow{B}$$
(dechlorination)

$$\overline{CF_2-CF_2-O-CClF-CF_2} \xrightarrow{C}$$
(cyclization)

$$CHF_2-CF_2-O-CClF-CClF_2 \xrightarrow{D}$$
$$CHF_2-CF_2-O-CHF-CHF_2$$
(hydrogenation)

$$\begin{array}{l} CF_2-CF_2-O-CClF_2 \\ | \\ CF_2-CF_2-O-CClF_2 \end{array}$$
and/or
$$\begin{array}{l} CF_2-CClF-O-CF_2CF_2Br \\ | \\ CF_2-CClF-O-CF_2CF_2Br \end{array}$$
(coupling)

Furthermore, in its turn the desired product, according to the above scheme (A) can undergo a hydrogenation, with the byproduct $$CHF_2CF_2O-CF=CF_2$$

being formed.

Such metals as Zn, traditionally used in dehalogenation reactions, turned out to be poorly suitable for the above mentioned specific reaction (the "A" step).

Surprisingly, it has now been discovered (in accordance with the present invention) that the dechlorination of $$CBrF_2-CF_2-O-CClF-CClF_2$$

takes place in the presence of Cu when an aprotic solvent is used, which consists or consists essentially of an aliphatic amide of the formula

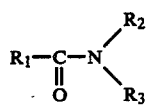

wherein
$R_1$ and $R_2$ are, independently of each other, either H or ($C_1$-$C_2$)-alkyl groups, and
$R_3$ is a ($C_1$-$C_2$)-alkyl group.

Therefore, the object of the present invention is a process for preparing

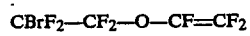

comprising the dehalogenation of

in the presence of Cu and of an apolar aprotic solvent consisting or consisting essentially of the above aliphatic amides. In particular, the solvent is preferably used under anhydrous conditions; in fact, it has been demonstrated that when aliphatic amides containing more than 500 ppm of water are used, the undesired products as above specified (the "C" step) can be obtained, with the reaction yields being consequently lowered.

Therefore the anhydrous conditions of the solvent and of the reaction medium can provide a measure of the purity of the obtained PFBEVE, once the above secondary reactions are prevented from taking place by using a suitable metal/solvent pair.

Among the aliphatic amides suitable for the purpose of the present invention, monomethyl-formamide, dimethyl-formamide, monoethyl-formamide, diethyl-formamide, dimethyl-acetamide, and dimethyl-propionamide may be cited. However, dimethylformamide and dimethylacetamide are particularly preferred for the purposes of the present invention.

The specificity of the above reaction is even more surprising if one considers that the use of such alkali-metal salts as NaI or NaF and $K_2CO_3$, customarily used respectively as the catalyst and as a buffer for the free acidity in the reactions of dechlorination of perfluoroalkyl-vinyl-ethers, turn out to be harmful, causing the dechlorination reaction to be completly blocked.

Several metal/solvent pairs were tested, which turned out to be poorly effective in the reaction of dechlorination according to the present invention.

In fact, when protic solvents (alcohols) were used, independently from the metal, a very high yield of the hydrogenated product and the complete absence of bromoethyl-vinyl-ether resulted.

On the contrary, when aprotic solvents different from the hereinabove defined aliphatic amides were used, an extremely low conversion and a very low reactivity were observed. For example, dimethylformamide, effective according to the present invention in the presence of copper, turned out to be an unsuitable solvent when used with such other metals as Sn, Mg and Zn, in that, although high conversion rates were obtained, the selectivity to PFBEVE turned out to be low owing to the formation of large amounts of hydrogenated products.

Although for the purposes of the present invention any type of commercial copper of any size may be used, electrolytic type copper in the form of a very fine powder is preferably used.

The reaction temperature is a function of the boiling point of the reaction mixture, and in case DMFA is used, such temperature is within the range of from 100° up to 160° C., and is preferably within the range of from 130° up to 150° C.

The amount of solvent added to the reaction medium is not critical. In any case, good homogenization of the catalyst powder and of the reactant mass should be employed.

The reaction time may be within the range of from 40 minutes up to 60 minutes, and is not a critical parameter of the present invention.

The process according to the present invention makes it possible for perfluoro-(2-bromoethyl-vinyl-ether) to be prepared with very good yields.

As indicated above, this compound is of considerable interest in the industrial field, and is especially useful as a comonomer in the preparation of fluoropolymers thanks to its ability to introduce active sites in the processes of vulcanization of the peroxy type.

The following examples are reported for the purpose of still better illustrating the invention, but without limiting it.

EXAMPLE 1

To a 250 ml glass reactor, 50 ml of DMFA with a low water content (40 ppm) is charged, with stirring, and then 11 g of an extremely fine powder of electrolytic copper is gradually added. After homogenizing the whole mass, the heating of the reaction mixture is started until a temperature of 80°-100° C. inside the kettle is reached.

At this point 30 g of

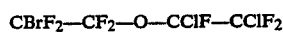

dissolved in a further 50 ml of DMFA is added. After an induction time of about 45-60 minutes, and at the kettle temperature of 135° C. the vapors of

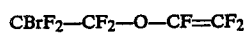

start to be released and, after being condensed by the overhead condenser, are drawn off and subjected to gas-chromatographic analysis.

25 g of a mixture is recovered which, after being washed with water in order to remove dimethylformamide, upon gas-chromatographic analysis, shows the following molar composition:

| | |
|---|---|
| $CBrF_2$—$CF_2$—O—CF=$CF_2$ | 65% |
| $CHF_2$—$CF_2$—O—CClF—$CClF_2$ | 0.5% |
| unreacted $CBrF_2$—$CF_2$—O—CClF—$CClF_2$ | 34.5% |

The conversion is hence 65.5% by mol, and the selectivity to perfluoro-(2-bromoethyl-vinyl-ether) is more than 98% by mol.

EXAMPLE 2

To the same reactor as in the preceding test, and under the same reaction conditions, dimethylformamide containing approximately 0.6% of water is used.

At the end of the test, after water washing, 20 g of an organic mixture is recovered which, upon gas-chromatographic analysis, shows the following molar composition:

| | |
|---|---|
| $CBrF_2-CF_2-O-CF=CF_2$ | 20% |
| $CHF_2-CF_2-O-CClF-CClF_2$ | 38% |
| unreacted $CBrF_2-CF_2-O-CClF-CClF_2$ | 40% |

The conversion is hence 60% by mol, and the selectivity is about 35% by mol.

EXAMPLE 3

To the same reactor as in the preceding tests, dimethylformamide with a water content of approximately 500 ppm is used.

The reaction temperature is kept constant at 145° C.

At the end of the test, after water washing, an organic mixture is recovered, which upon gas-chromatographic analysis, shows the following molar composition:

| | |
|---|---|
| $CBrF_2-CF_2-O-CF=CF_2$ | 50% |
| $CHF_2-CF_2-O-CClF-CClF_2$ | 9% |
| unreacted $CBrF_2-CF_2-O-CClF-CClF_2$ | 40% |

The conversion of the starting product is 60% and the selectivity with respect to PFBEVE is higher than 85%.

EXAMPLE 4

To a 250 ml glass reactor, 30 ml of N,N-dimethylacetamide is charged with stirring and then 7.5 g of an extremely fine powder of electrolytic copper is gradually added. After homogenizing the whole mass, the heating of the reaction mixture is started until a temperature of 80°–100° C. inside the kettle is reached.

At this point 23 g of $CBrF_2-CF_2-O-CClF-CClF_2$ dissolved in a further 25 ml of N,N-dimethylacetamide is slowly added. After an induction time of about 45–60 minutes, and at the kettle temperature of 165° C., vapors of $CBrF_2-CF_2-O-CF=CF_2$ start to be released and, after being condensed by the overhead condenser, are drawn off and subjected to gas-chromatographic analysis.

15 g of a mixture is recovered which, after being washed with water in order to remove N,N-dimethylacetamide, upon gas-chromatographic analysis shows the following molar composition:

| | |
|---|---|
| $CBrF_2-CF_2-O-CF=CF_2$ | 20% |
| $CHF_2-CF_2-O-CClF-CClF_2$ | 1.5% |
| unreacted $CBrF_2-CF_2-O-CClF-CClF_2$ | 78.5% |

The conversion is hence 21.5% and the selectivity with respect to perfluoro-(2-bromoethyl-vinyl-ether) is about 93% by mol.

EXAMPLE 5 (COMPARATIVE EXAMPLE)

Under the same conditions, and to the same reactor as in Example 1, 18 g of a powder of electrolytic Cu and
5 g of $K_2CO_3$ dried at 120° C. for 15 hours,
dissolved in 120 ml of dimethylformamide with a low water content (40 ppm), were charged.
To them:
50 g of $CBrF_2-CF_2-O-CClF-CClF_2$ dissolved in 50 ml of DMFA was slowly added.

An organic mixture was recovered which, when analysed by gas-chromatography, showed the following molar composition:

| | |
|---|---|
| $CBrF_2-CF_2-O-CF=CF_2$ | 1% |
| $CHF_2-CF_2-O-CClF-CClF_2$ | 4% |
| unreacted $CBrF_2-CF_2-O-CClF-CClF_2$ | 95% |

EXAMPLE 6 (COMPARATIVE EXAMPLE)

Under the same conditions, and to the same reactor as in Example 1,
2.5 g of a powder of electrolytic Cu, and
5 g of NaI dried at 120° C. for 15 hours,
dissolved in 10 ml of anhydrous dimethylformamide, were charged.
To them:
10 g of $CBrF_2-CF_2-O-CClF-CClF_2$ dissolved in 10 ml of DMFA was slowly added.

7 g of an organic mixture is recovered which, when analysed by gas-chromatography, showed the following molar composition:

| | |
|---|---|
| $CBrF_2-CF_2-O-CF=CF_2$ | 1% |
| $CHF_2-CF_2-O-CClF-CClF_2$ | 2% |
| unreacted $CBrF_2-CF_2-O-CClF-CClF_2$ | 97% |

The conversion is hence 3%.

EXAMPLE 7 (COMPARATIVE EXAMPLE)

Under the same conditions, and to the same reactor as in Example 1,
4.5 g of a powder of electrolytic Cu and
1 g of NaF dried at 120° C. for 15 hours,
dissolved in 25 ml of anhydrous dimethylformamide, are charged.
To them:
20 g of $CBrF_2-CF_2-O-CClF-CClF_2$ dissolved in 25 ml of DMFA, was slowly added.

18 g of an organic mixture is recovered which, when analysed by gas-chromatography, showed the following molar composition:

| | |
|---|---|
| $CBrF_2-CF_2-O-CF=CF_2$ | 1.2% |
| $CHF_2-CF_2-O-CClF-CClF_2$ | 0.8% |
| unreacted $CBrF_2-CF_2-O-CClF-CClF_2$ | 98% |

The conversion is hence 2%.

EXAMPLE 8 (COMPARATIVE EXAMPLE)

By operating according to the same procedures as in the preceding examples, several metal/solvent pairs were used in order to evaluate their selectivity with respect to PFBEVE.

The characteristics of the reaction and the results are reported in the following Table:

TABLE

| Metal Solvent Pair | Metal Reactant Molar Ratios | Temperature | Conversion, % by mol | Products |
| --- | --- | --- | --- | --- |
| Zn/DMFA | 1.3 | 150° | 50 | 3% PFBEVE |
| Mg/DMFA | 1.3 | 150° | 20 | Byproducts |
| Sn/DMFA | 1.7 | 150° | 50 | Byproducts |
| Pt/DMFA | 1.0 | 150° | 0 | 0 |
| Zn/DMSO | 1.1 | 100° | 10 | Byproducts |
| Sn/dioxane | 1.5 | 100° | 5 | Byproducts |
| Cu/dioxane | 1.8 | 100° | 4 | Byproducts |
| Cu/acrylonitrile | 2.0 | 80° | 0 | 0 |
| Cu/cyclohexane | 2.0 | 160° | 0 | 0 |

What is claimed is:

1. Process for preparing perfluoro-(2-bromoethyl-vinyl-ether) comprising the dehalogenation of 2-bromo-1',2'-dichloro-perfluoro-diethyl-ether in the presence of metallic copper as a catalyst and of an aprotic solvent consisting essentially of an aliphatic amide of the formula

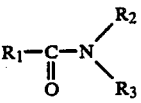

wherein
$R_1$ and $R_2$ are, independently of each other, either H or $(C_1-C_2)$-alkyl groups, and
$R_3$ is a $(C_1-C_2)$-alkyl group.

2. Process for preparing perfluoro-(2-bromoethyl-vinyl-ether) according to claim 1, further characterized in that the aliphatic amide has a water content not higher than 500 ppm.

3. Process according to claim 2, wherein the water content of the aliphatic amide is about 40 ppm.

4. Process for preparing perfluoro-(2-bromoethyl-vinyl-ether) according to claim 1, further characterized in that the reaction temperature is within the range of from 100° C. up to 160° C.

5. Process according to claim 1, wherein the copper is electrolytic copper.

6. Process according to claim 1, wherein the copper is in the form of an extremely fine copper powder.

7. Process according to any one of claims 1 to 6, wherein the aliphatic amide is selected from the group consisting of monomethyl-formamide, dimethyl-formamide, monoethyl-formamide, diethyl-formamide, dimethyl-acetamide, and dimethyl-propionamide.

8. Process according to one of claims 1 to 6, wherein the aliphatic amide is dimethylformamide.

9. Process according to any one of claims 1 to 6, wherein the aliphatic amide is dimethylacetamide.

* * * * *